United States Patent
Moore

(10) Patent No.: US 7,486,761 B2
(45) Date of Patent: Feb. 3, 2009

(54) COMPUTED TOMOGRAPHY FACILITATION METHOD AND APPARATUS

(75) Inventor: John F. Moore, Libertyville, IL (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/683,642

(22) Filed: Mar. 8, 2007

(65) Prior Publication Data

US 2008/0219403 A1    Sep. 11, 2008

(51) Int. Cl.
*A61B 6/03* (2006.01)
*G01N 23/00* (2006.01)

(52) U.S. Cl. .......................................... 378/9; 378/19

(58) Field of Classification Search ............... 378/4, 378/9, 55, 57, 98, 8, 56, 62, 177, 197, 198, 378/208, 19, 98.8
See application file for complete search history.

(56) References Cited

U.S. PATENT DOCUMENTS

| | | | |
|---|---|---|---|
| 5,023,895 A | 6/1991 | McCroskey et al. | |
| 5,946,371 A | 8/1999 | Lai | |
| 6,018,562 A * | 1/2000 | Willson | 378/9 |
| 6,411,670 B1 | 6/2002 | Besson | |
| 6,901,131 B2 * | 5/2005 | Edic et al. | 378/19 |
| 7,039,153 B2 * | 5/2006 | Bruder et al. | 378/9 |
| 7,254,211 B2 * | 8/2007 | Hunt et al. | 378/20 |
| 2002/0085681 A1 * | 7/2002 | Jensen | 378/197 |

FOREIGN PATENT DOCUMENTS

WO        9905967        2/1999

OTHER PUBLICATIONS

Wang, GE, X-Ray Micro-CT With A Displaced Detector Array, Medical Physics, vol. 29, No. 7, Jul. 2002, pp. 1634-1636.

* cited by examiner

*Primary Examiner*—Irakli Kiknadze
(74) *Attorney, Agent, or Firm*—Fitch, Even, Tabin & Flannery

(57) ABSTRACT

A first X-ray detector (203) is positioned to detect at least the X-rays that intersect the center of rotation (201) for an object (205) with respect to an X-ray source (202). A second X-ray detector (207) is then positioned to detect X-rays that do not overlap with the X-rays as are detected by the first X-ray detector as well as X-rays (210) that intersect a periphery of a circle (209) that circumscribes an outer extreme boundary (208) of the object to be scanned.

24 Claims, 4 Drawing Sheets

US 7,486,761 B2

COMPUTED TOMOGRAPHY FACILITATION METHOD AND APPARATUS

TECHNICAL FIELD

This invention relates generally to computed tomography and more particularly to offset rebinning processing.

BACKGROUND

Computed tomography is known in the art and comprises in some cases an approach to object imaging in which a thin X-ray beam (such as a fan beam) rotates around an object. Many small detectors measure the amount of X-rays that make it through the object and a computer then constructs a series of cross-sectional scans across a common axis.

A problem can arise when the object being scanned is larger than the relevant dimensions of the detector (allowing for geometrical magnification) in that portions of the object will not be adequately scanned. (It should be understood that, as used herein, "detector" refers to a device capable of providing multiple signals across a line, across several adjacent lines, or across an area as the case may be.) Offset rebinning represents a prior art approach to dealing with this problem. By this approach the detector is offset with respect to a line that intersects the X-ray source and the center of rotation about which the object and X-ray source/detector rotate with respect to one another. In general, such a placement has the detector extending to one side of this line. So configured, of course, no scanning data is obtained for the opposing side of the line. Rebinning, however, provides for capturing this missing data when the object and X-ray source/detector have later rotated 180 degrees. Simply put, offset rebinning permits at least one half of an object to be initially scanned with missing portions of the object being scanned 180 degrees later.

For at least some applications offset rebinning provides an adequate solution. Even when allowing for data feathering of the so-called forward and reverse data, the detector effectively becomes about 80% larger. That is, with offset rebinning, an object up to about 80% larger can be accommodated as compared to more typical third generation processing with the same detector. This is not to say, however, that offset rebinning has completely addressed all needs in this regard. A problem can occur, for example, when an object to be scanned is larger than that which can otherwise be accommodate by an offset rebinning approach.

In such a case, a typical thought might be to simply use a larger detector and/or to chain multiple detectors together in an abutted fashion. Unfortunately, it may be impractical and/or commercially impossible to obtain a larger detector. Similarly, satisfactory results are ordinarily not obtained by abutting two or more detectors against one another, as several types of detectors, such as but not limited to image intensifiers and flat-plate detector arrays, cannot be abutted without incurring a certain amount of dead space between their active detection areas. Such a configuration, for example, typically leaves a coverage gap of at least some size between adjacent detectors. This gap, in turn, yields scanning results that suffer from undesirable artifacts, ambiguity, and the like.

BRIEF DESCRIPTION OF THE DRAWINGS

The above needs are at least partially met through provision of the computed tomography facilitation method and apparatus described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, a first X-ray detector is positioned to detect at least the X-rays that intersect the center of rotation for an object with respect to an X-ray source. A second X-ray detector is then positioned to detect X-rays that do not overlap with the X-rays as are detected by the first X-ray detector as well as X-rays that intersect a periphery of a circle that circumscribes an outer extreme boundary of an object to be scanned in the object scanning space.

By one approach these X-ray detectors are offset with respect to a line that intersects both the X-ray source and the center of rotation. By one approach, more than one X-ray source can be employed. If desired, a third (or more) X-ray detector can be additionally provided. By one approach, this additional detector (s) is positioned between the aforementioned first and second X-ray detector.

So configured, these X-ray detectors and source(s) are used in conjunction with a 360 degree offset rebinning process to thereby develop a substantially complete computed tomography data set of the object in question. The unique geometry, spacing, and alignment of the X-ray detectors serves to substantially avoid the creation of unwanted artifacts while also tending to ensure that the object is fully and completely scanned. These teachings will readily facilitate satisfactory scanning of an object that is considerably larger than can be achieved via the aforementioned prior art approaches. Those skilled in the art will appreciate that these teachings also readily permit this beneficial leveraging of existing offset rebinning calculation techniques and processing without requiring extensive or invasive alteration of that processing.

Figure 1:
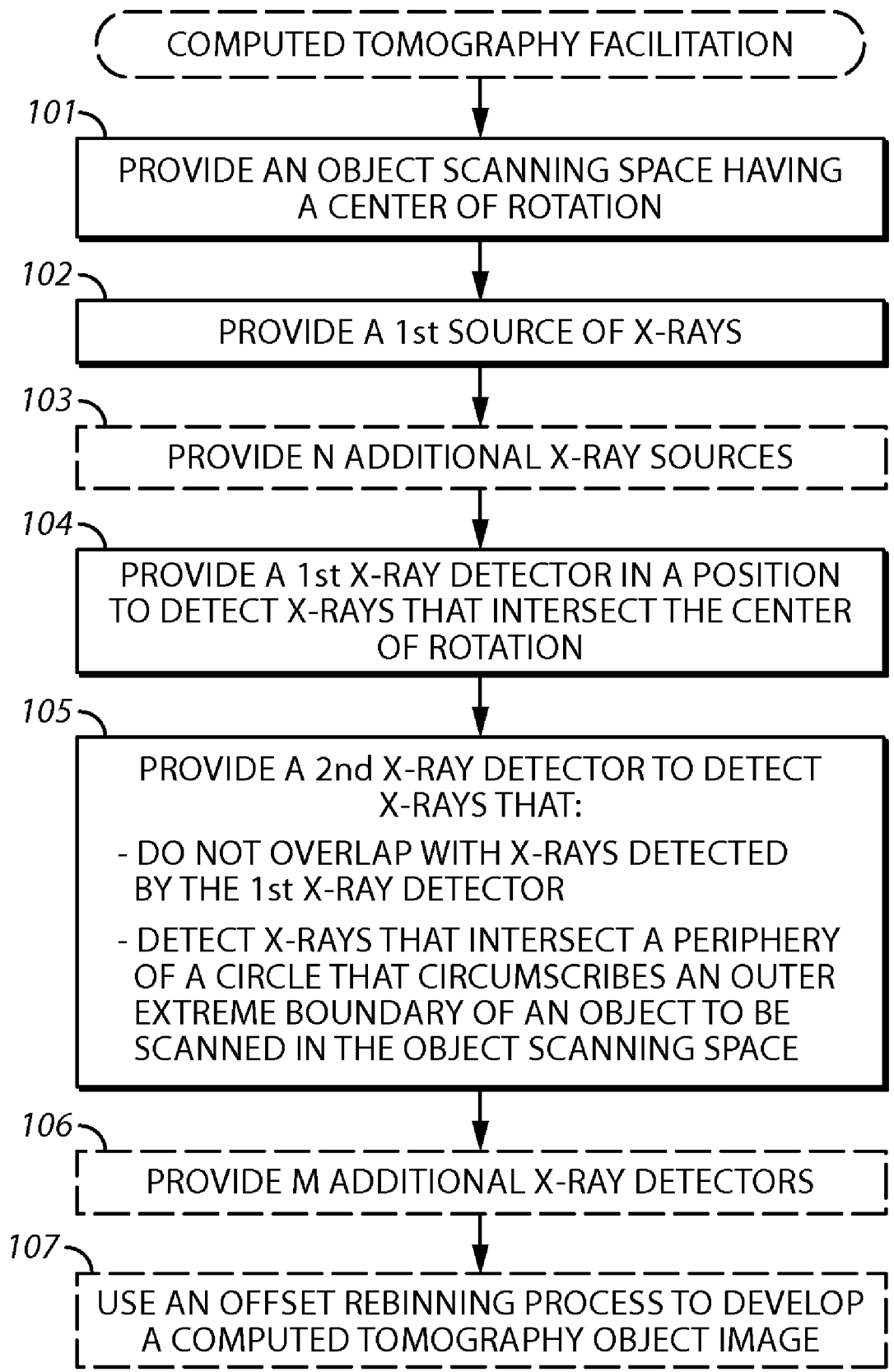
FIG. 1 comprises a flow diagram as configured in accordance with various embodiments of the invention.

These and other benefits may become clearer upon making a thorough review and study of the following detailed description. Referring now to the drawings, and in particular to FIG. 1, an illustrative process 100 provides 101 an object scanning space having a center of rotation. This object scanning space may be of any desired size and will typically be of sufficient size to receive and accommodate an object of interest that is to be scanned. In systems where the X-ray source emits a fan beam, this space typically includes a cross-section of the object that consists of one or a few "slices." In the case where the X-ray source emits a cone beam, this space typically includes a volume portion of the object, including possibly the entire object. The center of rotation comprises a relative center of rotation. Accordingly, these teachings are compatible for use with an object that rotates, for example, on a turntable while the corresponding object scanning equipment remains in a fixed position. These teachings are also compatible for use with object scanning equipment that rotates about a fixed position object. And, if desired, these teachings may also be used in an application setting where both the object and the object scanning equipment are each capable of independent rotation. Such an object scanning space is well understood in the art and therefore, for the sake of brevity, further elaboration in this regard will not be presented here.

This process 100 then provides 102 a first source of X-rays. By one approach this first source of X-rays provides a so-called fan beam of X-rays. Depending upon the needs and/or limitations as may characterize a given application setting, this fan beam can be horizontally aligned, vertically aligned, or aligned with respect to any other orientation of interest. Various X-ray sources are known in the art and others will no doubt be developed hereafter. As these teachings are not particularly sensitive to the selection of any particular X-ray source, additional details regarding such X-ray sources need not set forth here. (If desired, and as will be discussed below in more detail, N additional X-ray sources may also be optionally provided 103 (where N comprises an integer of one or higher)).

This process 100 also provides 104 a first X-ray detector to be used in conjunction with the aforementioned first X-ray source. This first X-detector may be positioned to detect at least the X-rays that intersect the previously mentioned center of rotation. By one approach this can further comprise positioning the first X-ray detector in an offset position with respect to a line that intersects both the first source of X-rays and the center of rotation.

Figure 2:
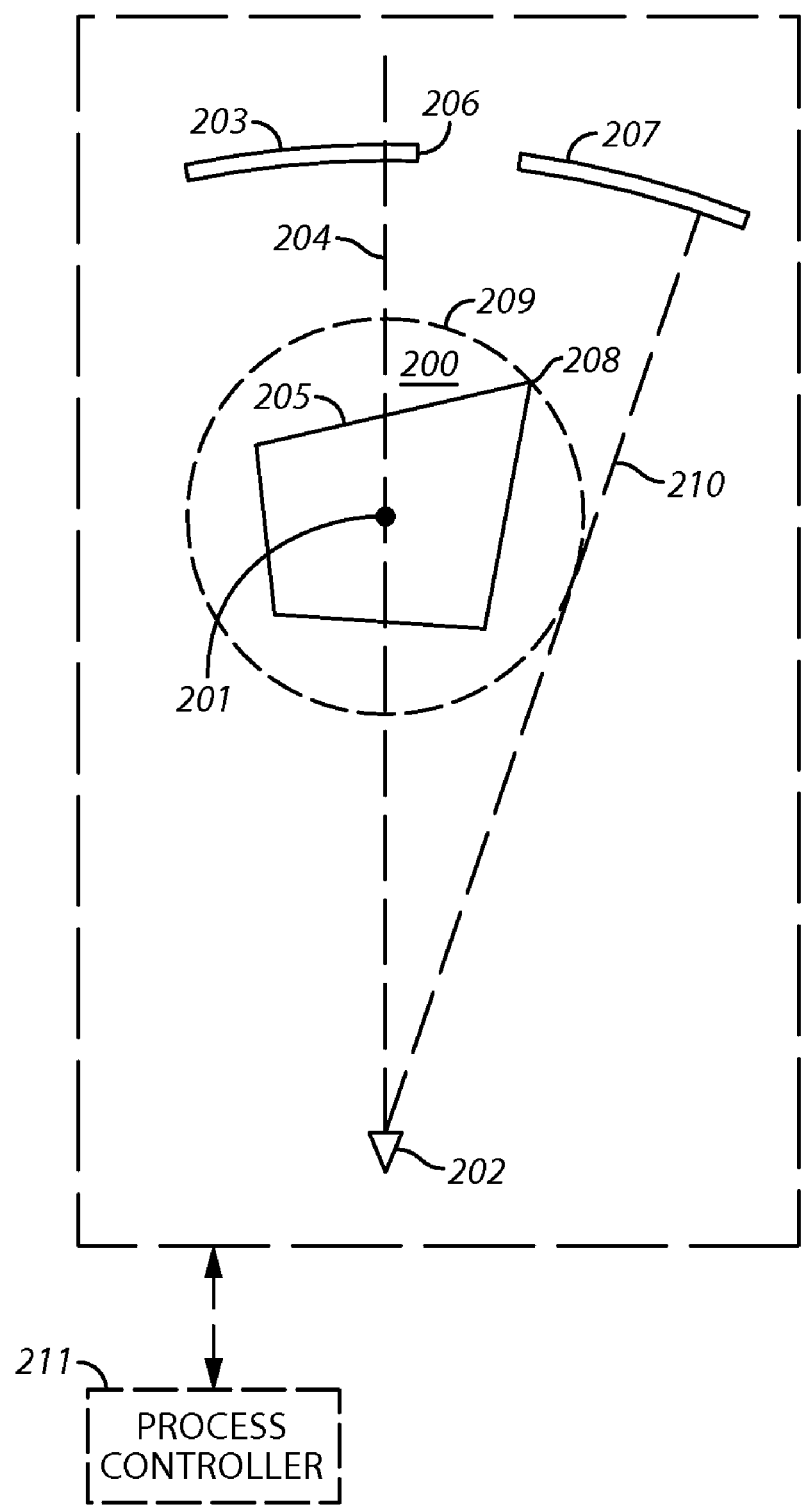
FIG. 2 comprises a top plan block diagram as configured in accordance with various embodiments of the invention.

To illustrate, and referring momentarily to FIG. 2, an object scanning space 200 having the above described center of rotation 201 features a first X-ray source 202 disposed on one side of an object 205 to be scanned and the above-mentioned first X-ray detector 203 on the opposing side of the object 205. More particularly, in this illustrative embodiment, this first X-ray detector 203 is offset with respect to a line 204 that intersects both the center of rotation 201 and the first X-ray source 202. By one approach, this first X-ray detector is offset such that one edge 206 of the first X-ray detector 203 extends only a relatively small distance (such as, for example, less than 10% of the total length of the first X-ray detector 203) beyond this line 204. In this particular illustrative example the first X-ray detector 203 is offset away from a second X-ray detector 207 that is described below in more detail.

Referring again to FIG. 1, this process 100 also provides 105 at least a second X-ray detector. By one approach, this second X-ray detector is positioned to detect X-rays that do not overlap with the X-rays as are detected by the first X-ray detector and also to detect at least the X-rays that intersect a periphery of a circle that circumscribes an outer extreme boundary of an object to be scanned in the object scanning space. To illustrate, and referring again momentarily to FIG. 2, the object 201 to be scanned can be seen to have an outermost boundary 208 that defines a corresponding circle 209 with respect to the center of rotation 201. The second X-ray detector 207, in this illustrative embodiment, is positioned to ensure that an X-ray path 210 that tangentially intersects the periphery of that circle 209 is detectable by that second X-ray detector 207.

Either or both of these X-ray detectors may comprise, for example, a flat plate detector, an image intensifier, and so forth as are known in the art. By one approach, these detectors comprise multi-channel detectors having an overall width that is inadequate to cover at least half of the object scanning space.

Figure 3:
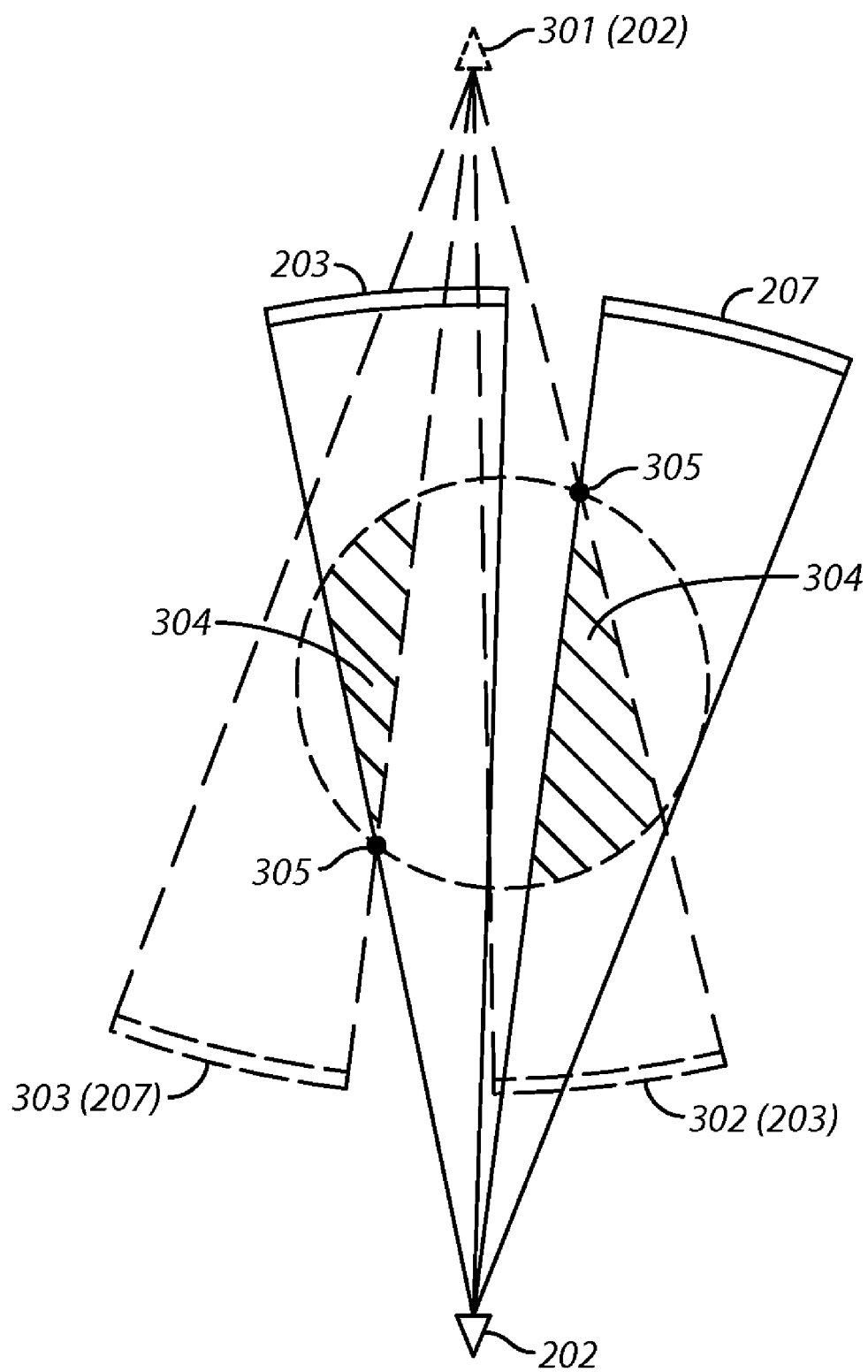
FIG. 3 comprises a top plan block diagram as configured in accordance with various embodiments of the invention.

So configured, a complete set of object scan data can be developed by scanning the object 205 while causing rotation through 360 degrees as between the object 205 and the aforementioned X-ray source/detectors. With momentary reference to FIG. 3, when the X-ray source 202 and X-ray detectors 203 and 207 are positioned as initially shown above, only a portion of the object scanning space 200 is scanned. Similarly, when these elements have rotated 180 degrees to the positions denoted by reference numerals 301, 302, and 303, again only a portion of the object scanning space 200 is scanned. By capturing scan data through 360 degrees of relative rotation, however, a complete set of scan data for an object in the object scanning space 200 can be reliably developed.

In some cases, depending upon parameters such as the size of the X-ray detectors, the angular width of the X-ray beam, and the applicable magnification factor, some amount of redundant information may result. In the illustrative example shown, the two areas shown with crosshatching and denoted by reference numeral 304 comprise such areas. Through 360 degrees of scanning this redundant data will represent a cylindrical ring (presuming a three dimensional scanning process) and can be used, for example, during subsequent data processing to reduce the influence of noise by well-known methods involving, for example, weighted averaging. In addition, the overlap region may be used to enhance spatial resolution in a manner similar to the technique sometimes called "quarter-detector shift," where the paths of the rays from the source to some detectors partially or fully fill in the spaces between other paths.

The locations denoted by reference numerals 305 may be relevant in at least some application settings. These locations mark a point at the periphery of the aforementioned circle where the outer edges of the first and second X-ray detectors intersect one another when in opposing positions (for example, the point of intersection between the outer detection edge of the first X-ray detector 203 when in the first described position and the inner detection edge of the second X-ray detector 207 when in the second described position 303). If the X-ray detectors are too small, and/or the spacing between the two X-ray detectors is too large, small uncovered triangle-shaped artifacts may appear in the resultant data as corresponds to these locations. Such a concern can be at least partially ameliorated by reducing the magnification and/or increasing the distance between the X-ray source and the detectors to present a lower angular beam-width.

Figure 4:
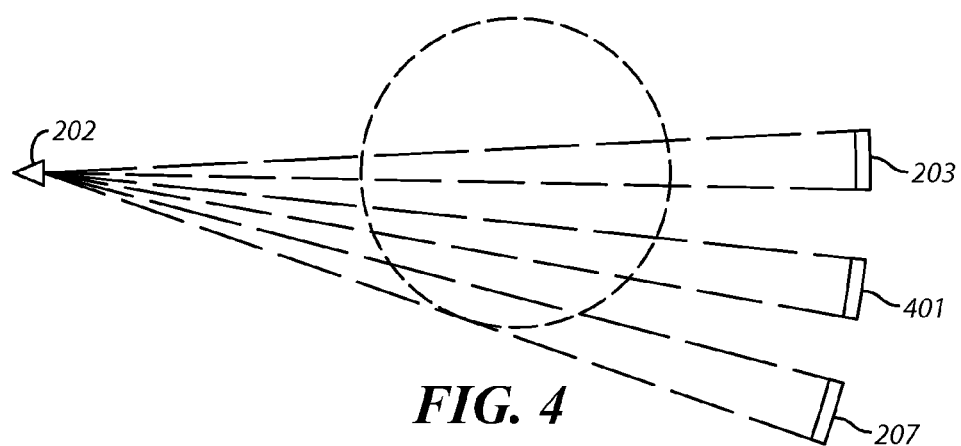
FIG. 4 comprises a top plan block diagram as configured in accordance with various embodiments of the invention.

Referring again to FIG. 1, if desired, this process 100 can accommodate the optional provision 106 of additional X-ray detectors beyond the two already mentioned above. As one illustrative example in this regard, and referring momentarily to FIG. 4, a third X-ray detector 401 can be positioned between the first X-ray detector 203 and the second X-ray detector 207 mentioned above. By one approach this additional X-ray detector is positioned so as to not abut or otherwise be placed too close to the other X-ray detectors.

As noted earlier, this process 100 can also accommodate the provision 103 of a plurality of X-ray sources if so desired.

Figure 5:
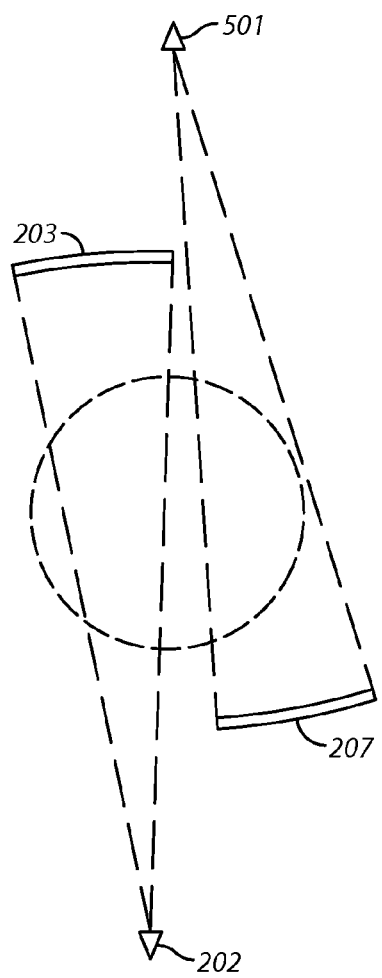
FIG. 5 comprises a top plan block diagram as configured in accordance with various embodiments of the invention.

To illustrate, and referring momentarily to FIG. 5, a second source of X-rays 501 can be positioned on an opposite side of the object scanning space from the first X-ray source 202. In this particular illustrative example the second X-ray detector 207 is disposed on a side of the object scanning space that is opposite the second X-ray source 501. Again, notwithstanding this orientation, the second X-ray detector 207 is positioned to otherwise meet the stipulations set forth above in this regard. As a practical matter, effective X-ray shielding must usually be interposed between the second source and the nearby detector.

Referring again to FIG. 1, and notwithstanding which configuration one might chose as regards the relative number and/or positioning of the X-ray source(s) and X-ray detectors, an offset rebinning process as is otherwise known in the art can be used 107 with the resultant computed tomography platform to develop a computed tomography image of any object in the object scanning space. As noted, this may comprise capturing image data during at least 360 degrees of relative rotation as between the object and the first and second X-ray detectors.

Those skilled in the art will appreciate that the above-described process is readily enabled using any of a wide variety of available and/or readily configured platforms, including partially or wholly programmable platforms as are known in the art or dedicated purpose platforms as may be desired for some applications. Referring to FIG. 2, for example, a process controller 211 can be configured and arranged, via, for example, appropriate programming, to so use the described apparatus to capture a substantially complete set of image data for the object by capturing image data during 360 degrees of relative rotation and to conduct this offset rebinning process with respect to that captured image data.

So configured, those skilled in the art will appreciate that detectors that are individually incapable of capturing even one half of a given object are nevertheless usable in tandem to achieve capture of a fully representative data set. This data set, in turn, is usable to facilitate the generation of a substantially artifact-free resultant scanned image (wherein the expression image shall be understood to refer to a two or three dimensional portrayal, a projection, or the like).

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

I claim:

1. A method comprising:
   providing an object scanning space having a center of rotation;
   providing at least a first source of X-rays;
   providing a first X-ray detector in a position to detect at least the X-rays that intersect the center of rotation;
   providing at least a second X-ray detector in a position to detect the X-rays that:
      do not overlap with the X-rays as are detected with the first X-ray detector; and
      detect at least the X-rays that intersect a periphery of a circle that circumscribes an outer extreme boundary of an object to be scanned in the object scanning space;
   wherein all of the X-ray detectors as are provided are insufficient to make a complete scan of the object scanning space without providing some relative motion as between the X-ray detectors and the object scanning space;
   further comprising providing a second source of X-rays wherein the first source of X-rays and the second source of X-rays are substantially opposite one another and wherein providing a first X-ray detector comprising disposing the first X-ray detector in a position that is opposite the first source of X-rays and providing a second X-ray detector comprises disposing the second X-ray detector in a position that is opposite the second source of X-rays.

2. The method of claim 1 wherein providing a first X-ray detector comprises providing a flat plate detector.

3. The method of claim 1 wherein providing a first X-ray detector comprises providing an image intensifier.

4. The method of claim 1 wherein providing a first X-ray detector comprises providing a multi-channel detector of width inadequate to cover at least half of the object scanning space.

5. The method of claim 1 wherein:
   providing a first X-ray detector comprises providing a flat plate detector;
   providing a second X-ray detector comprises providing a flat plate detector.

6. The method of claim 1 wherein:
   providing a first X-ray detector comprises providing an image intensifier;
   providing a second X-ray detector comprises providing an image intensifier.

7. The method of claim 1 wherein:
   providing a first X-ray detector comprises providing a multi-channel detector of width inadequate to cover at least half of the object scanning space;
   providing a second X-ray detector comprises providing a multi-channel detector of width inadequate to cover at least half of the object scanning space.

8. The method of claim 1 wherein providing a first X-ray detector in a position to detect at least the X-rays that intersect the center of rotation comprises positioning the first X-ray detector in an offset position with respect to a line that intersects both the first source of X-rays and the center of rotation.

9. The method of claim 8 wherein positioning the first X-ray detector in an offset position with respect to a line that intersects both the first source of X-rays and the center of rotation comprises positioning the first X-ray detector such that one edge of the first X-ray detector extends only a relatively small distance beyond the line that intersects both the first source of X-rays and the center of rotation and towards the second X-ray detector.

10. A method comprising:
    providing an object scanning space having a center of rotation;
    providing at least a first source of X-rays;
    providing a first X-ray detector in a position to detect at least the X-rays that intersect the center of rotation;
    providing at least a second X-ray detector in a position to detect the X-rays that:
       do not overlap with the X-rays as are detected with the first X-ray detector; and
       detect at least the X-rays that intersect a periphery of a circle that circumscribes an outer extreme boundary of an object to be scanned in the object scanning space;
    using an offset rebinning process with the first and second X-ray detector to develop a computed tomography image of an object in the object scanning space.

11. The method of claim 10 wherein providing a first X-ray detector and providing a second X-ray detector comprises providing both the first X-ray detector and the second X-ray detector on a same side of the object scanning space and opposite the first source of X-rays.

12. The method of claim 10 wherein using the offset rebinning process with the first and second X-ray detector to develop a computed tomography image of an object in the object scanning space further comprises capturing a complete set of image data for the object by capturing image data during 360 degrees of relative rotation as between the object and the first and second X-ray detectors.

13. An apparatus comprising:
an object scanning space having a center of rotation;
a first source of X-rays;
a first X-ray detector that is disposed in a position to detect at least the X-rays that intersect the center of rotation;
at least a second X-ray detector that is disposed in a position to detect the X-rays that:
  do not overlap with a majority of the X-rays as are detected with the first X-ray detector; and
  detect at least the X-rays that intersect a periphery of a circle that circumscribes an outer extreme boundary of an object to be scanned in the object scanning space;
wherein all of the X-ray detectors as are disposed in a position to detect the X-rays are insufficient to make a complete scan of the object scanning space without providing some relative motion as between the X-ray detectors and the object scanning space;
further comprising:
a second source of X-rays; and
wherein the first source of X-rays and the second source of X-rays are disposed substantially opposite one another and wherein the first X-ray detector is disposed in a position that is opposite the first source of X-rays and the second X-ray detector is disposed in a position that is opposite the second source of X-rays.

14. The apparatus of claim 13 wherein the first X-ray detector comprises a flat plate detector.

15. The apparatus of claim 13 wherein the first X-ray detector comprises an image intensifier.

16. The apparatus of claim 13 wherein the first X-ray detector comprises a multi-channel detector of width inadequate to cover at least half of the object scanning space.

17. The apparatus of claim 13 wherein:
the first X-ray detector comprises a flat plate detector; and
the second X-ray detector comprises a flat plate detector.

18. The apparatus of claim 13 wherein:
the first X-ray detector comprises an image intensifier; and
the second X-ray detector comprises an image intensifier.

19. The apparatus of claim 13 wherein:
the first X-ray detector comprises a multi-channel detector of width inadequate to cover at least half of the object scanning space;
the second X-ray detector comprises a multi-channel detector of width inadequate to cover at least half of the object scanning space.

20. The apparatus of claim 13 wherein the first X-ray detector is disposed in an offset position with respect to a line that intersects both the first source of X-rays and the center of rotation.

21. The apparatus of claim 20 wherein the first X-ray detector is disposed such that one edge of the first X-ray detector extends only a relatively small distance beyond the line that intersects both the first source of X-rays and the center of rotation and towards the second X-ray detector.

22. An apparatus comprising:
an object scanning space having a center of rotation;
a first source of X-rays;
a first X-ray detector that is disposed in a position to detect at least the X-rays that intersect the center of rotation;
at least a second X-ray detector that is disposed in a position to detect the X-rays that:
  do not overlap with a majority of the X-rays as are detected with the first X-ray detector; and
  detect at least the X-rays that intersect a periphery of a circle that circumscribes an outer extreme boundary of an object to be scanned in the object scanning space;
a process controller that is configured and arranged to use the apparatus to conduct an offset rebinning process with the first and second X-ray detectors to develop a computed tomography image of an object in the object scanning space.

23. The apparatus of claim 22 wherein both the first X-ray detector and the second X-ray detector are disposed on a same side of the object scanning space and opposite the first source of X-rays.

24. The apparatus of claim 22 wherein the process controller is further configured and arranged to use the apparatus to conduct an offset rebinning process with the first and second X-ray detector to develop a computed tomography image of an object in the object scanning space by capturing a complete set of image data for the object by capturing image data during 360 degrees of relative rotation as between the object and the first and second X-ray detectors.

* * * * *

UNITED STATES PATENT AND TRADEMARK OFFICE
CERTIFICATE OF CORRECTION

PATENT NO. : 7,486,761 B2
APPLICATION NO. : 11/683642
DATED : February 3, 2009
INVENTOR(S) : John F. Moore It is certified that error appears in the above-identified patent and that said Letters Patent is hereby corrected as shown below:

Title Page item 73 should read -

Assignee: Varian Medical Systems, Inc., Palo Alto, CA (US)

Signed and Sealed this

Twenty-first Day of April, 2009

JOHN DOLL
*Acting Director of the United States Patent and Trademark Office*